(12) United States Patent
Quigley et al.

(10) Patent No.: US 11,435,332 B2
(45) Date of Patent: Sep. 6, 2022

(54) SENSOR OFFSET DIAGNOSTIC IN IDLE AND AFTER-RUN

(71) Applicant: GM Global Technology Operations LLC, Detroit, MI (US)

(72) Inventors: David P. Quigley, Brighton, MI (US); Sarah Funk, Canton, MI (US); Kevin J. McKay, New Hudson, MI (US); Scott R. Zechiel, Ypsilanti, MI (US); Ruggiero Chiariello, Turin (IT)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 0 days.

(21) Appl. No.: 17/032,551

(22) Filed: Sep. 25, 2020

(65) Prior Publication Data

US 2022/0099642 A1 Mar. 31, 2022

(51) Int. Cl.
*G01N 33/00* (2006.01)
*G01M 15/10* (2006.01)

(52) U.S. Cl.
CPC ........ *G01N 33/007* (2013.01); *G01M 15/102* (2013.01)

(58) Field of Classification Search
CPC ........ F01N 3/208; F01N 11/00; F01N 3/2066; F01N 2560/026; F01N 2560/14; F01N 2900/0404; F02D 41/0275; F02D 41/146; F02D 41/024; F02D 41/1441; F02D 41/222; F02D 2041/1432; G01M 15/102; G01N 33/007; G01N 33/0037; Y02T 10/24

See application file for complete search history.

(56) References Cited

U.S. PATENT DOCUMENTS

| 7,610,142 | B1* | 10/2009 | Hoard | F01N 13/008 60/274 |
| 2011/0252767 | A1* | 10/2011 | Lin | F02D 41/146 60/274 |
| 2016/0369677 | A1* | 12/2016 | Ponnathpur | B01D 53/9495 |
| 2017/0241321 | A1* | 8/2017 | Yoo | F01N 11/00 |

* cited by examiner

*Primary Examiner* — John Fitzgerald
*Assistant Examiner* — Truong D Phan
(74) *Attorney, Agent, or Firm* — Vivacqua Crane, PLLC

(57) ABSTRACT

A method for reducing sensor noise in an automobile vehicle NOx sensor offset diagnostic includes: connecting an exhaust system to an engine of an automobile vehicle; sensing a condition of the exhaust system using at least one NOx sensor; identifying when the at least one NOx sensor is at a low noise condition; and running a diagnostic to identify conditions of the at least one NOx sensor. The method further includes selecting one of the low noise condition as the engine in an after-run condition or as the engine in an engine idle condition.

16 Claims, 4 Drawing Sheets

SENSOR OFFSET DIAGNOSTIC IN IDLE AND AFTER-RUN

INTRODUCTION

The present disclosure relates to nitrogen oxide sensors and diagnostics for monitoring nitrogen oxide sensors in automobile vehicles.

A nitrogen oxide sensor or NOx sensor is a high-temperature device which detects nitrogen oxides in combustion environments such as an automobile vehicle or a truck tailpipe. NOx gases are known to cause smog and acid rain and are therefore limited in automobile exhaust systems. Diesel engines produce higher engine-out NOx emissions than spark-ignition gasoline engines do. Selective catalytic reduction (SCR) has therefore been developed and when available allows a diesel engine to emit similar values of NOx at a tailpipe compared to a typical gasoline engine.

One method of minimizing NOx emissions is to first detect NOx emissions and then employ a feedback loop in a combustion process to minimize NOx production by combustion optimization or regeneration of NOx traps. NOx sensors are used to detect NOx emissions and are monitored using diagnostics to detect poor SCR catalyst efficiency and an offset to NOx sensor signal (among many other NOx sensor diagnostics required by regulation). SCR catalyst efficiency is often detected using measured efficiency via two NOx sensors, one upstream and one downstream of the SCR. Another requirement is to detect a missing SCR catalyst (where catalyst may be called a "brick", and this diagnostic may also be called "empty can"). Because the NOx sensor is cross sensitive to NH3, NH3 slip from the SCR during transient conditions with an SCR catalyst present or under any operating conditions with a missing SCR catalyst can result in false failures of the downstream NOx sensor offset diagnostic. Alternatively, depending on the order in which SCR catalyst and NOx sensor diagnostics are run/arbitrated, a missing SCR catalyst may result in erroneous detection of a high sensor offset. NH3 slip from the SCR during a transient operation and in any conditions with a missing SCR brick can result in false failures in the downstream NOx sensor offset diagnostic unless the failure threshold is set very high (>300 ppm). In many cases, controls and diagnostics performance are compromised to satisfy the competing requirements. In addition, an empty SCR can *may produce a false failure of NOx sensor offset when an SCR NOx catalyst efficiency is below a predetermined threshold (e.g., a P20EE event). However, if the NOx offset monitor runs and fails first, the NOx sensor is de-activated and the P20EE fault cannot run.

It is currently desirable to run NOx sensor diagnostics during overrun (non-fueling) conditions. This is done because the engine is not generating emissions under these conditions and the sensors should theoretically read zero NOx once stabilized. Depending on the drive cycle, however, non-fueling events may not be long enough for NOx sensor stabilization. An additional issue with maintaining repetitive NOx sensor diagnostics is a lack of availability to run diagnostics during the overrun (non-fueling) conditions due in part to the multiple other diagnostics that must be run during this time which take higher operating priority.

Thus, while current NOx sensor diagnostics achieve their intended purpose, there is a need for a new and improved system and method for NOx sensor offset diagnostics in conditions outside of overrun.

SUMMARY

According to several aspects, an automobile vehicle sensor offset diagnostic system includes an engine. An exhaust system is connected to the engine. At least one sensor senses a condition of the exhaust system. A diagnostic is run to identify conditions of the at least one sensor at a low noise condition.

In another aspect of the present disclosure, the low noise condition defines a vehicle after-run condition of the engine.

In another aspect of the present disclosure, the low noise condition defines a stable condition of operation defining a vehicle low idle condition.

In another aspect of the present disclosure, the vehicle low idle condition is with an engine rpm approximately 1200 rpm or less.

In another aspect of the present disclosure, the at least one sensor defines a NOx sensor.

In another aspect of the present disclosure, a signal from the NOx sensor is compared to a NOx model directly or to a scalar/map or table of expected NOx at an idle condition.

In another aspect of the present disclosure, an electronic control module using at least one sensor signal from the NOx sensor to calculate a reductant dosing set point and communicate the setpoint to control operation of a reductant dosing system.

In another aspect of the present disclosure, the at least one sensor defines an engine out NOx sensor.

In another aspect of the present disclosure, the at least one sensor further defines a selective catalytic reduction (SCR) catalyst out NOx sensor monitoring a condition of the SCR catalyst.

In another aspect of the present disclosure, multiple enablement criteria are provided, wherein all of the enablement criteria are confirmed prior to initiation of the diagnostic.

According to several aspects, a method for reducing sensor noise in an automobile vehicle sensor offset diagnostic includes: connecting an exhaust system to an engine of an automobile vehicle; sensing a condition of the exhaust system using at least one sensor; and running a diagnostic to identify conditions of the at least one sensor when the at least one sensor is at a low noise condition.

In another aspect of the present disclosure, the method further includes confirming the engine is in an after-run condition prior to performing the running the diagnostic step.

In another aspect of the present disclosure, the method further includes activating the diagnostic based on predetermined enablement criteria assessed prior to a vehicle key-off.

In another aspect of the present disclosure, the method further includes applying an integral approach for running the diagnostic, including: receiving a NOx sensor value defining an (x) value; retrieving an offset value defining a (y) value, the offset value defining either a NOx model value or an expected NOx value identified in a table of expected NOx values; subtracting either the NOx model value or the expected NOx value from the NOx sensor value to identify a real offset value; identifying if the real offset value is greater than a predetermined acceptable offset map value; wherein: if the real offset value is greater than the predetermined acceptable offset map value the real offset value is integrated; or if the real offset value is NOT greater than the predetermined acceptable offset map value no further integration action is performed.

In another aspect of the present disclosure, the method further includes confirming the engine is in an engine idle condition prior to performing the running the diagnostic step.

In another aspect of the present disclosure, the method further includes limiting the engine idle condition to an engine rpm of approximately 1200 rpm or less.

In another aspect of the present disclosure, the method further includes applying an incremental x/y approach for running the diagnostic, including: receiving a NOx sensor value defining an (x) value; retrieving an offset value defining a (y) value, wherein the offset value defines either a NOx model value or an expected NOx value in a table of expected NOx values; subtracting one of the NOx model value or the expected NOx value from the NOx sensor value to identify a real offset value; identifying if the real offset value is greater than a predetermined offset threshold; wherein: if the real offset value is greater than the predetermined offset threshold the (x) and (y) values are incremented in an incrementing step until both values meet predetermined calibrated values; or if the real offset value is NOT greater than the predetermined offset threshold only the (y) value is incremented.

According to several aspects, a method for reducing sensor noise in an automobile vehicle NOx sensor offset diagnostic, includes: connecting an exhaust system to an engine of an automobile vehicle; sensing a condition of the exhaust system using at least one NOx sensor; identifying when the at least one NOx sensor is at a low noise condition; and running a diagnostic to identify conditions of the at least one NOx sensor.

In another aspect of the present disclosure, the method further includes selecting the low noise condition as the engine in an after-run condition.

In another aspect of the present disclosure, the method further includes selecting the low noise condition as the engine in an engine idle condition.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
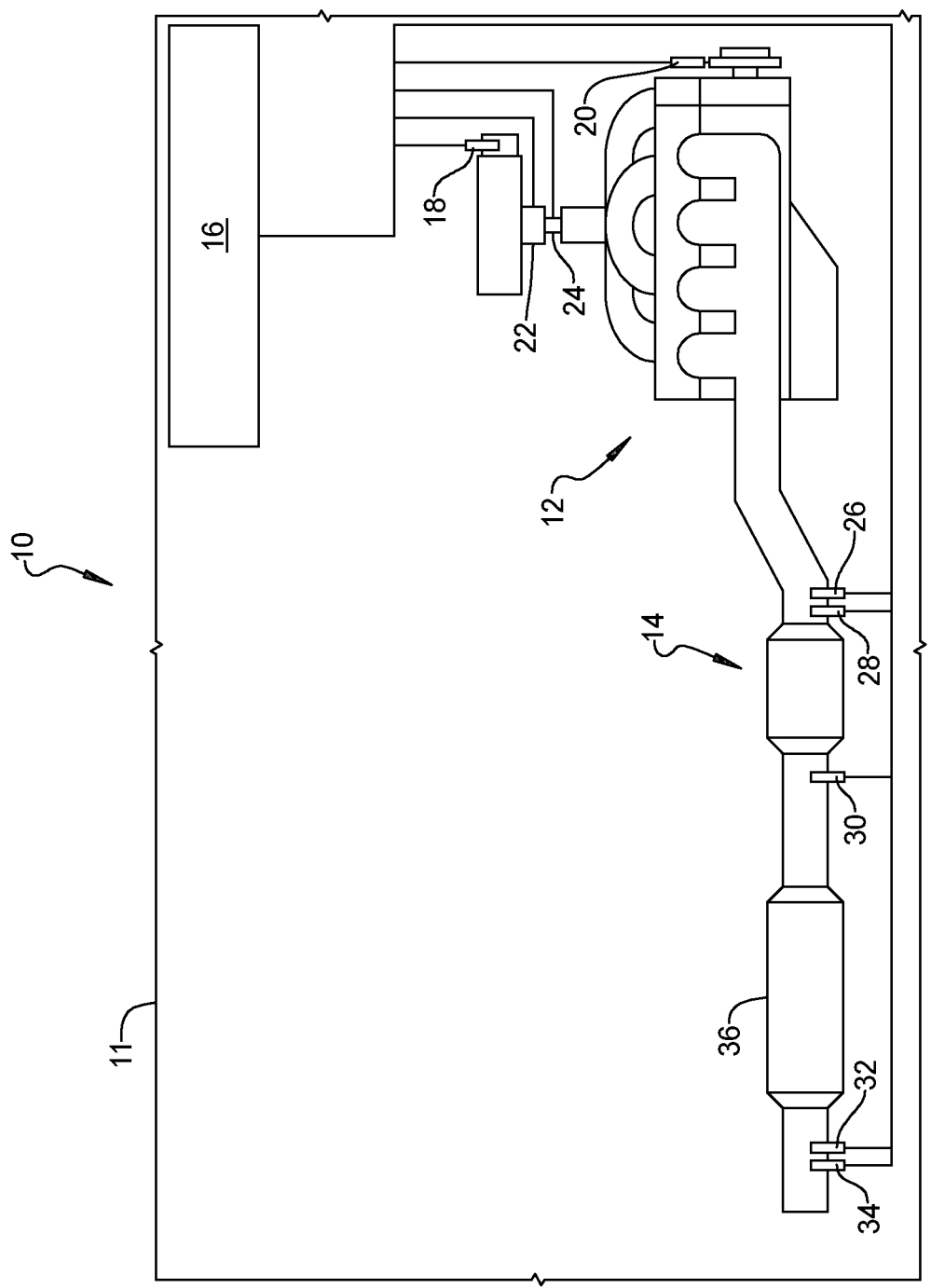
FIG. 1 is a diagram of an automobile vehicle having a system and method for sensor diagnostic offset according to an exemplary aspect.

Referring to FIG. 1, a system and method for sensor offset diagnostic 10 for an automobile vehicle 11 includes a combustion engine 12 such as a diesel engine which exhausts gases including NOx into an exhaust system 14. An electronic control module 16 receives sensory signals from multiple sensors provided with the engine 12 and the exhaust system 14 and controls operation of the engine 12. The multiple sensors may include but are not limited to a mass air flow sensor 18, an engine speed sensor 20, an intake air temperature sensor 22, a throttle position sensor 24, an engine out NOx sensor 26, multiple exhaust temperature sensors 28, 30, 32 and a selective catalytic reduction (SCR) catalyst out NOx sensor 34 which monitors the condition of an SCR catalyst 36.

Selective catalytic reduction of NOx may use urea or ammonia as a reductant to reduce NOx emissions. In the SCR process, NOx reacts with the reductant, which may also be pure anhydrous ammonia or aqueous ammonia, and/or urea, which is injected into the exhaust gas stream before or upstream of the SCR catalyst 36. The electronic control module 16 uses one or more sensor signals, including a signal from the engine out NOx sensor 26 and the SCR catalyst out NOx sensor 34, to calculate a reductant dosing set point and communicate the setpoint, such as a voltage level, to control operation of a reductant dosing system.

For a diagnostic to be run in an after-run condition defined as an engine stopped or shut-off condition it is necessary to first identify the engine 12 has been running to allow the diagnostic to be run. The enablements and disablements are identified which permit the diagnostic to be run. For example the NOx sensor 26 can read NOx and ammonia ($NH_3$) and is therefore cross sensitive to both NOx and ammonia. Ammonia ($NH_3$) is therefore used as a reductant to convert NOx to $H_2O$ and $N_2$. As one exemplary enablement for the present system and method in after-run condition, if a high temperature is measured upstream of the NOx sensor 26 during operation, the high temperature will cause ammonia to release, or slip, from the SCR catalyst. If this condition occurs within approximately 60 seconds of engine shut-off, the diagnostic if run is expected to fail and will therefore not be enabled. Multiple enablements and disablements for operation of the diagnostic of the present disclosure are identified below.

Referring to FIG. 2 and again to FIG. 1, a flow diagram of the system and method for sensor diagnostic offset 10 identifies method steps for running a sensor offset diagnostic 38 in the automobile vehicle 11 in an after-run condition in lieu of in an overrun (non-fueling) condition. The electronic control module 16 is programmed to perform the steps to run the sensor offset diagnostic 38. The method for running a sensor offset diagnostic 38 initially performs an engine running check 40 to identify if the engine 12 has been running to prequalify criteria for performance of an after-run diagnostic to follow. If a response to the engine running check 40 is a yes signal 42, an enablement-criteria met step 44 is next performed to identify if a predetermined set of enablement criteria are met. If a response to the enablement-criteria met step 44 is a no signal 46, the method for running the sensor offset diagnostic 38 returns to the engine running check 40.

If all criteria pre-specified in the enablement-criteria met step 44 are confirmed which is indicated by an enablement-criteria met YES signal 47, a confirmation is conducted that the engine 12 is now off in an engine off confirmation step 48. After confirming the engine is off and the enablement-criteria are met, a diagnostic run step 50 is performed. The program may also directly move to the diagnostic run step 50 in a bypass step 52, bypassing the engine off confirmation step 48. Following the diagnostic run step 50 a test result is identified in a test result determination step 54. If the test result determination step 54 produces a diagnostic pass result 56 the method for running the sensor offset diagnostic 38 returns to the engine running check 40. If the test result determination step 54 produces a diagnostic fail result 58 the method for running the sensor offset diagnostic 38 is reset in a set DTC step 60 and the program ends.

Figure 2:
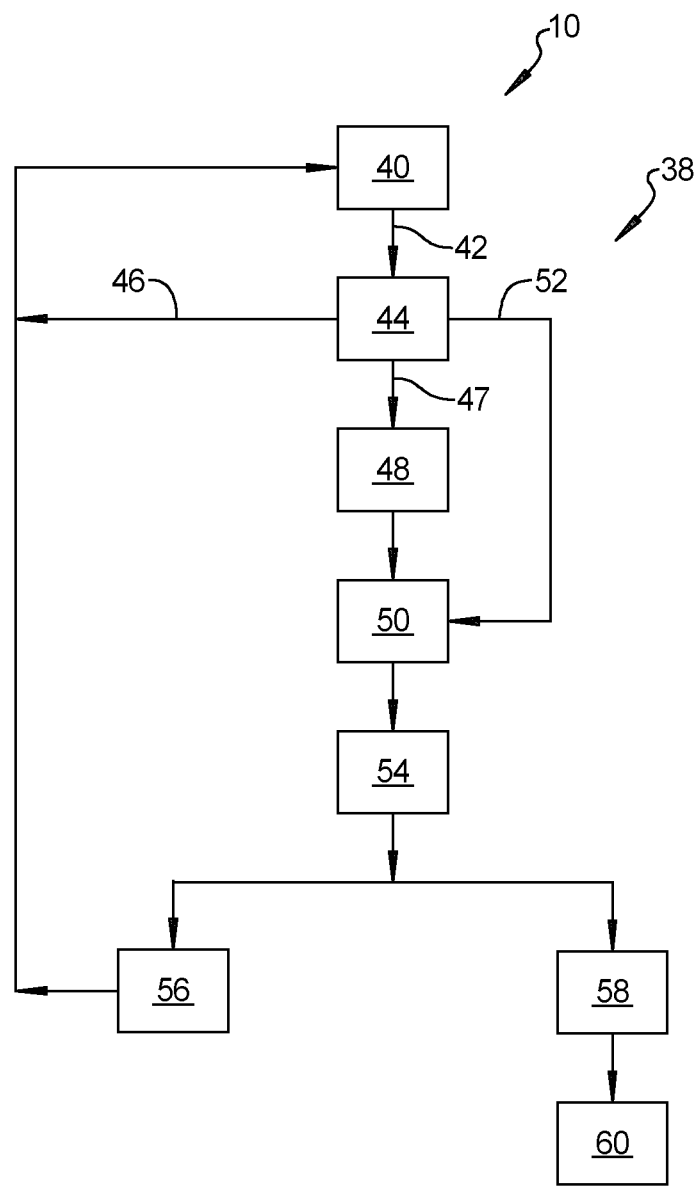
FIG. 2 is a flow diagram of the steps for performing a first method for performing the sensor diagnostic offset of the system of FIG. 1.

Referring to FIG. 3 and again to FIG. 2, in another aspect, in lieu of the sensor offset diagnostic 38 being performed in an after-run condition a sensor offset diagnostic 62 is run during an engine idle condition, again rather than in the overrun condition where sensor offset/response diagnostics are typically run. Similar to the results produced in the after-run condition, engine out NOx levels at idle condition are also low and substantially stable, thus the sensor signals are low and substantially stable. Because the sensor offset diagnostic 62 is run at idle condition the NOx sensor signal may be compared to a NOx model directly and/or to a scalar/map or table of expected NOx at idle condition, which results in a more robust diagnostic. According to several aspects the idle condition defines an engine operation with no direct driver input to control an engine speed or an engine operation at or below approximately 1200 rpm, however system of the present disclosure is not limited to a specific idle rpm or rpm range.

Figure 3:
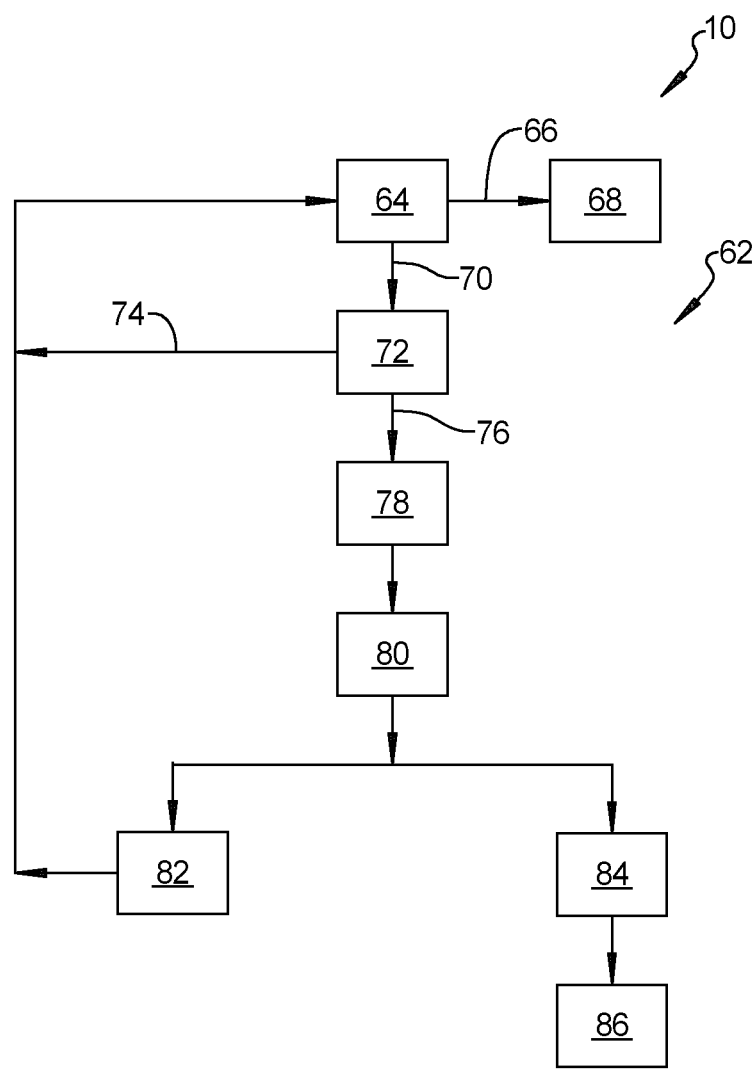
FIG. 3 is a flow diagram of the steps for performing a second method for performing the sensor diagnostic offset of the system of FIG. 1.

With continuing reference to FIG. 3, the sensor offset diagnostic 62 is similar to the sensor offset diagnostic 38 and initially performs an engine at-idle check 64 to identify if the engine 12 has been idling to prequalify criteria for performance of an engine idle diagnostic to follow. If a response to the engine at-idle check 64 is a NO signal 66 the program ends. If a response to the engine at-idle check 64 is a YES signal 70, an enablement-criteria met step 72 is next performed to identify if a predetermined set of enablement criteria are met. If a response to the enablement-criteria met step 72 is a no signal 74, the method for running the sensor offset diagnostic 62 returns to the engine at-idle check 64.

If all criteria pre-specified in the enablement-criteria met step 72 are confirmed which is indicated by an enablement-criteria met YES signal 76. After confirming the engine is at idle and the enablement-criteria are met, a diagnostic run step 78 is performed. Following the diagnostic run step 78 a test result is identified in a test result determination step 80. If the test result determination step 80 produces a diagnostic pass result 82 the method for running the sensor offset diagnostic 62 returns to the engine at-idle check 64. If the test result determination step 80 produces a diagnostic fail result 84 the method for running the sensor offset diagnostic 62 is reset in a set DTC step 86 and the program ends.

Figure 4:
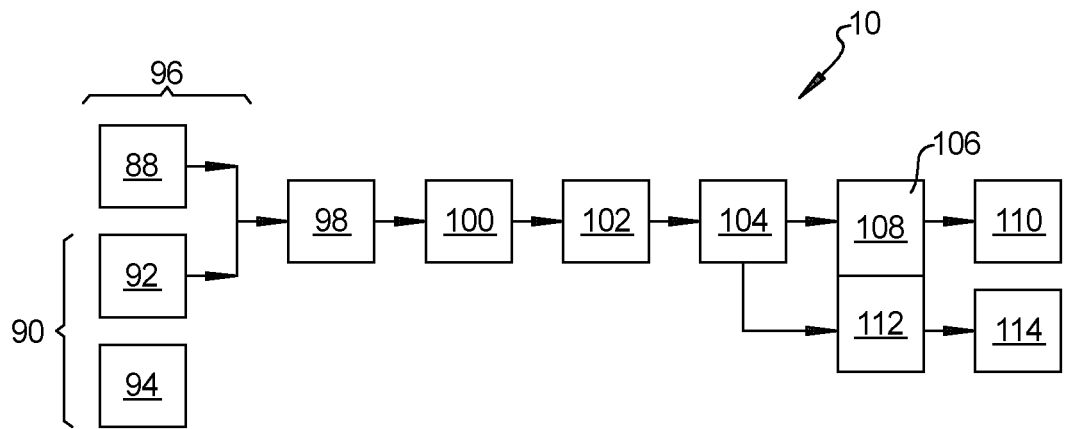
FIG. 4 is a flow diagram of the steps for performing an x/y approach for performing the sensor diagnostic offset of the system of FIG. 3.

Referring to FIG. 4 and again to FIGS. 2 and 3, an incremental x/y approach is presented for running the sensor offset diagnostic 62 described above during engine idle conditions. In the incremental x/y approach a NOx sensor value 88 is received defining an (x) value. An offset value 90 is then retrieved defining a (y) value. The offset value 90 may be either a NOx model value 92 or an expected NOx value 94 identified for example in a table of expected NOx values. In a combining operation 96 either the NOx model value 92 or the expected NOx value 94 is subtracted from the NOx sensor value 88 in a subtractor 98 to identify a real offset value 100. A determination 102 is then conducted to identify if the real offset value 100 is greater than a predetermined offset threshold 104.

In an option step 106 when the real offset value 100 is greater than the predetermined offset threshold 104 in a first option 108 the (x) and (y) values are incremented in an incrementing step 110 until both values meet predetermined calibrated values. Alternatively, as a second option 112 or an ELSE option if the real offset value 100 is NOT greater than the predetermined offset threshold 104 only the (y) value is incremented. Once the (x) and/or the (y) values meet the calibrated values, the DTC passes or fails depending on a predetermined quantity of fails.

Figure 5:
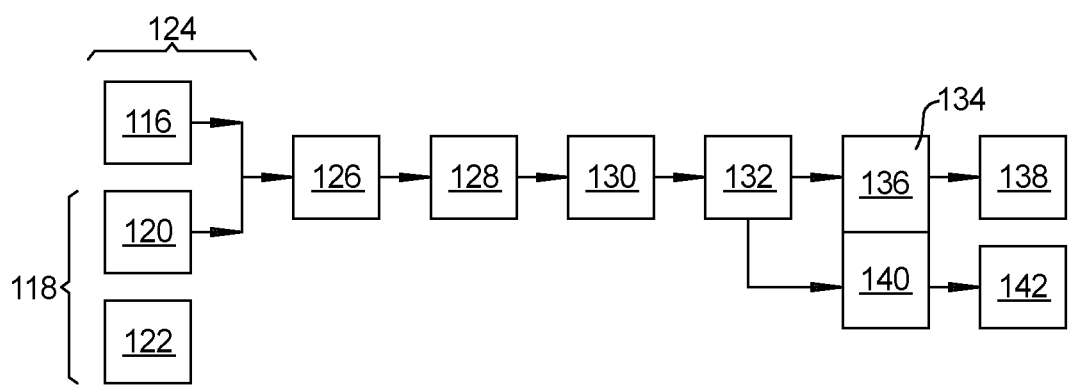
FIG. 5 is a flow diagram of the steps for performing an integral approach for performing the sensor diagnostic offset of the system of FIG. 3.

Referring to FIG. 5 and again to FIGS. 1 through 4, an integral approach is presented for running the sensor offset diagnostic 62 described above during engine idle conditions. In the integral approach a NOx sensor value 116 is received defining an (x) value. An offset value 118 is then retrieved defining a (y) value. The offset value 118 may be either a NOx model value 120 or an expected NOx value 122 identified for example in a table of expected NOx values. In a combining operation 124 either the NOx model value 120 or the expected NOx value 122 is subtracted from the NOx sensor value 116 in a subtractor 126 to identify a real offset value 128. A determination 130 is then conducted to identify if the real offset value 128 is greater than a predetermined acceptable offset map value 132.

In an option step 134 when the real offset value 128 is greater than the predetermined acceptable offset map value 132 in a first option 136 the real offset value 128 is integrated in an integration step 138. Alternatively, as a second option 140 or an ELSE option if the real offset value 128 is NOT greater than the predetermined acceptable offset map value 132 in a step 142 no further integration action is performed. Once the real offset value 128 is greater than a predetermined threshold, the DTC fails.

As noted above in the enablement-criteria met step 44 for the method described in reference to FIG. 2, multiple enablements and disablements for operation of the diagnostic of the present disclosure are provided. The diagnostic will NOT run in after-run under the following exemplary conditions, but is not limited to the following conditions as conditions may be calibratable:

1) if the engine is or was stopped in DPF Regeneration mode or was in a calibratable debounced time after regeneration mode has stopped.
2) if the engine is or was stopped within a calibratable debounce time after the vehicle has seen a speed change in the negative direction above a calibratable threshold.
3) if the engine is or was stopped at low idle and the engine has been at low idle for longer than a calibrated time.
4) if the engine is or was stopped within a calibratable debounce time after the derivative of the SCR upstream temperature has exceeded a calibratable threshold. In double SCR brick systems this also applies to the SCR2 or second brick upstream temperature.
5) if the diagnostic is not enabled in the calibration.
6) if the diagnostic system is disabled.
7) if the Nox sensor is not present and the dew point is released.
8) if the engine is cranking.
9) unless the engine speed was within a calibratable range when it was running.
10) if the engine is in calibratable combustion mode(s) and if it is within a calibratable debounce time since leaving the combustion mode.
11) unless the exhaust mass flow is within a calibratable range when the engine was running and will be disabled/debounced for a calibratable time if it is out of that range.

12) unless the SCR temperature was within a calibratable range when the engine was running and will be disabled/debounced for a calibratable time if it is out of that range.
13) unless the DEF dosing is within a calibratable range when the engine was running and will be disabled/debounced for a calibratable time if it is out of that range.
14) unless the NH3 estimate on the brick is within a calibratable range when the engine was running and will be disabled/debounced for a calibratable time if it is out of that range.
15) if the vehicle is operating at high elevation (above approximately 12,000 feet), wherein open loop urea transient dosing is used.
16) if the vehicle is operating at ambient temperatures below approximately −11 degrees Centigrade, defining a temperature at or below which urea may freeze.

All of the above enablements/disablements for operation of the diagnostic apply to a second SCR brick as well if the application has two SCRs or multiple bricks in the architecture.

The present diagnostic concept when run in after-run or during idle eliminates the interaction between NH3 slip and sensor offset diagnosis. This is accomplished by conducting the diagnostic of the sensor when the sensor is exposed to the least system "noise", such as at idle condition when temperatures and NH3 slip are stable or least susceptible to rapid change, and in after-run when the engine is off. To ensure robust detection of sensor offset, diagnostic enablement criteria are therefore assessed while the engine is still running. Running the NOx sensor offset diagnostic in after-run or during idle will also decouple the interaction between offset NOx sensor faults and SCR efficiency and missing catalyst (empty can) diagnostics.

An automobile vehicle sensor offset diagnostic of the present disclosure offers several advantages. These include an improved diagnostic concept as an enabler for (1) improved emissions compliance, (2) more robust SCR efficiency diagnosis, and (3) lower emissions bin levels. Running the diagnostic in after-run may eliminate noise and variation in test results due to the elimination of engine operating conditions impact and interaction with other diagnostics, thus improving diagnostic robustness. Running the diagnostic at idle conditions may eliminate noise and variation in test results by minimizing engine operating conditions impact and interaction with other diagnostics, thus improving diagnostic robustness. The present diagnostic concept also increases robustness of sensor offset diagnosis. Improved robustness of catalyst efficiency and sensor offset diagnosis are in turn enablers for lower emissions standards.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A system for diagnosing a NOx sensor in a vehicle, the system comprising:
   a NOx sensor configured to sense a condition of an exhaust system;
   an electronic control module comprises a non-transitory computer readable recording medium storing a computer program product in electrical communication with the NOx sensor, wherein the electronic control module is programmed to:
   sense a condition of the exhaust system using the NOx sensor during an engine idle condition;
   run a diagnostic to identify conditions of the NOx sensor;
   confirm the engine is in the engine idle condition prior to running the diagnostic; and
   apply an incremental x/y approach for running the diagnostic, including:
   receive a NOx sensor value defining an (x) value;
   retrieve an offset value defining a (y) value, wherein the offset value further defines either a NOx model value or an expected NOx value in a table of expected NOx values;
   subtract one of the NOx model value or the expected NOx value from the NOx sensor value to identify a real offset value; and
   identify if the real offset value is greater than a predetermined offset threshold, wherein:
   if the real offset value is greater than the predetermined offset threshold, the (x) and (y) values are incremented in an incrementing step until the (x) and (y) values meet predetermined calibrated values; or
   if the real offset value is NOT greater than the predetermined offset threshold, the (y) value is incremented.

2. The system of claim 1, wherein the electronic control module is further programmed to:
   limit the engine idle condition to an engine rpm of approximately 1200 rpm or less.

3. The system of claim 1, wherein the electronic control module is further programmed to:
   activate the diagnostic based on predetermined enablement criteria assessed prior to a vehicle key-off.

4. The system of claim 3, wherein to perform the enablement criteria check, the electronic control module is further programmed to:
   determine the enablement criteria to be unsatisfied if the engine is cranking.

5. The system of claim 3, wherein to perform the enablement criteria check, the electronic control module is further programmed to:
   determine the enablement criteria to be unsatisfied if an exhaust mass flow is outside of a calibratable range.

6. The system of claim 3, wherein to perform the enablement criteria check, the electronic control module is further programmed to:
   determine the enablement criteria to be unsatisfied if a selective catalytic reduction (SCR) temperature is outside of a calibratable range.

7. The system of claim 3, wherein to perform the enablement criteria check, the electronic control module is further programmed to:
   determine the enablement criteria are to be unsatisfied if an $NH_3$ estimate on a brick is outside of a calibratable range.

8. The system of claim 3, wherein to perform the enablement criteria check, the electronic control module is further programmed to:
   determine the enablement criteria are to be unsatisfied if the vehicle is operating at ambient temperatures at or below which urea may freeze.

9. The system of claim 3, wherein to perform the enablement criteria check, the electronic control module is further programmed to:
   determine the enablement criteria to be unsatisfied if:
   the engine is cranking;

an exhaust mass flow is outside of an exhaust mass flow calibratable range;
a selective catalytic reduction (SCR) temperature is outside of an SCR temperature calibratable range;
an $NH_3$ estimate on the brick is outside of an $NH_3$ estimate on the brick calibratable range; and
the vehicle is operating at ambient temperatures at or below which urea may freeze.

10. A system for diagnosing a NOx sensor in an exhaust system connected to an engine in a vehicle, the system comprising:
a NOx sensor configured to sense a condition of an exhaust system;
an electronic control module comprises a non-transitory computer readable recording medium storing a computer program product in electrical communication with the NOx sensor, wherein the controller is programmed to:
perform an engine at-idle check;
perform an enablement criteria check if the engine is at idle;
perform a diagnostic run if the enablement criteria are satisfied, the diagnostic run including:
receive a sensor value from the NOx sensor;
retrieve an offset value;
subtract the offset value from the sensor value to identify a real offset value;
compare the real offset value to a threshold;
if greater than the threshold, incrementing the sensor value and the offset value until both values meet predetermined calibrated values;
if less than the threshold, incrementing only the offset value until the offset value meets the predetermined calibrated value;
determine a pass or a fail depending on a predetermined quantity of fails after the sensor value and the offset value meet the calibrated values.

11. The system of claim 10, wherein to perform the enablement criteria check, the electronic control module is further programmed to:
determine the enablement criteria to be unsatisfied if the engine is cranking.

12. The system of claim 10, wherein to perform the enablement criteria check, the electronic control module is further programmed to:
determine the enablement criteria to be unsatisfied if an exhaust mass flow is outside of a calibratable range.

13. The system of claim 10, wherein to perform the enablement criteria check, the electronic control module is further programmed to:
determine the enablement criteria to be unsatisfied if a selective catalytic reduction (SCR) temperature is outside of a calibratable range.

14. The system of claim 10, wherein to perform the enablement criteria check, the electronic control module is further programmed to:
determine the enablement criteria to be unsatisfied if an $NH_3$ estimate on a brick is outside of a calibratable range.

15. The system of claim 10, wherein to perform the enablement criteria check, the electronic control module is further programmed to:
determine the enablement criteria to be unsatisfied if the vehicle is operating at ambient temperatures at or below which urea may freeze.

16. The system of claim 10, wherein to perform the enablement criteria check, the electronic control module is further programmed to:
determine the enablement criteria to be unsatisfied if:
the engine is cranking;
an exhaust mass flow is outside of an exhaust mass flow calibratable range;
a selective catalytic reduction (SCR) temperature is outside of an SCR temperature calibratable range;
an $NH_3$ estimate on the brick is outside of an $NH_3$ estimate on the brick calibratable range; and
the vehicle is operating at ambient temperatures at or below which urea may freeze.

* * * * *